US006608195B2

(12) United States Patent
Rainville et al.

(10) Patent No.: US 6,608,195 B2
(45) Date of Patent: Aug. 19, 2003

(54) PROCESS FOR THE PREPARATION OF 2-(4-ALKYL-1-PIPERAZINYL)-BENZALDEHYDE AND -BENZYLIDENYL COMPOUNDS

(75) Inventors: Joseph P. Rainville, Uncasville, CT (US); Terry G. Sinay, Preston, CT (US); Stanley W. Walinsky, Mystic, CT (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 10/230,945

(22) Filed: Aug. 29, 2002

(65) Prior Publication Data

US 2003/0087914 A1 May 8, 2003

Related U.S. Application Data

(60) Provisional application No. 60/316,010, filed on Aug. 30, 2001.

(51) Int. Cl.$^7$ ...................... C07D 241/12; C07D 417/10
(52) U.S. Cl. ....................... 544/58.2; 544/395
(58) Field of Search ................................ 544/58.2, 39.5

(56) References Cited

FOREIGN PATENT DOCUMENTS

| WO | WO9814433 | 4/1998 |
|----|-----------|--------|
| WO | WO9925714 | 5/1999 |
| WO | WO9925715 | 5/1999 |

OTHER PUBLICATIONS

Heaton, et al., "Polyhalogenonitrobenzenes and Derived Compounds", J. Chem. Soc. Perkin Trans. 2, 1985, pp. 1275–1277, XP002217754.
Watthey, et al., XP002217753, "Synthesis and Biological Properties of Thiophene Ring Analogues of Mianserin", J. Med. Chem., 1983, pp. 1116–1122.
Nijhuis, et al., XP001118281, Two Step Synthesis of Hexahydropyrazino[1,2-α] pp 641–645. No Year of Pub.
Monge, et al., "Synthesis of 2–Piperazinylbenzothiazole", J. Med. Chem., vol. 37, 1994, pp 1320–1325, XP002217756.
J. Med. Chem., vol. 37, 1994, p. 1323, "Preparation of Compounds (2) and (7)".
Kreutzberger, et al., "Chlor–(1–piperazinyl)–1,3,5–Triazine", Arch. Pharm., 1988, pp. 837–840, XP002217758.
Arch. Pharm., 1988, pp. 838–839, "Preparation of Compounds, (3a)–(3c)".
Bader, et al., "Nucleophilic Displacement of Activated Fluorine in Aromatic Compounds", Journal of Organic Chemistry, vol. 31, 1966, pp. 2319–2321, XP002217757.
Journal of Organic Chemistry, vol. 31, 1966, p. 2321, "Preparation of 4–piperidino acetophenone".
Heaton, et al., "Polyhalogenitrobenzenes and Derived Compounds", Chem. Soc. Perkin Trans. 2, 1985, pp. 1275–1277, XP002217754.

Monge, et al., "Synthesis of 2–Piperazinylbenzothiazole and 2–Piperazinylbenzoxazole Derivatives with 5–HT3 Antagonist and 5–HT4 Agonist Properties", J. Med. Chem., vol. 37, 1994, pp1320–1325, XP002217756; p. 1323, "Preparation of Compounds (2) and (7)".
Kreutzberger, et al., "Chlor–(1–piperazinyl)–1,3,5–Triazine", Arch. Pharm., 1988, pp. 837–840, XP002217758; pp. 838–839, "preparation of compounds, (3a)–(3c)".
Bader, et al., "Nucleophilic Displacement of Activated Fluorine in Aromatic Compounds", Journal of Organic Chemistry, vol. 31, 1966, pp. 2319–2321, XP002217757; p. 2321, "Praparation of 4–piperidino acetophenone".
Watthey et al, "Synthesis and Biological Properties of Thiophene Ring Analogues of Mianserin," Journal of Medicinal Chemistry, vol. 26, 1983, pp. 1116–1122, XP002217753, pp. 1117 and 1121, preparation of compound 9a.
Nijhuis et al, "A Novel Two–Step Synthesis of Hexahydropyrazino(1,2–alpha)–quinolines", Synthesis, vol. 7, 1987, pp. 641–645, XP001118281, p. 642, preparation of compounds 5a–i.

(List continued on next page.)

*Primary Examiner*—John M. Ford
(74) *Attorney, Agent, or Firm*—P. C. Richardson; P. H. Ginsburg; A. D. Joran

(57) ABSTRACT

The present invention relates to a novel process for the preparation of a compound of formula I:

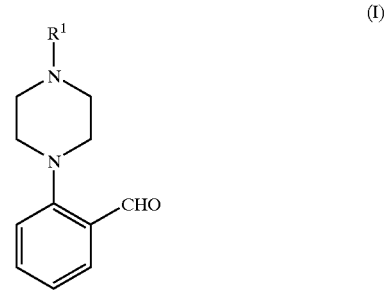

wherein $R^1$ is defined herein and compounds of formula II:

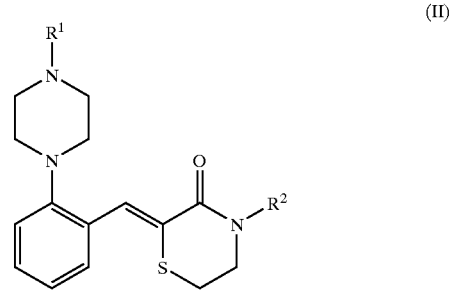

wherein $R^1$ and $R^2$ are defined herein. Said compound of formula I is useful in the treatment of various central nervous system disorders including depression.

21 Claims, No Drawings

OTHER PUBLICATIONS

Jeffrey W. H. Watthey, et al., "Synthesis and Biological Properties of Thiophene Ring Analogues of Mianserin", J. Med. Chem. 1988, 26, 1116–1222.

Walter H. N. Nijbuis, et al., "A Novel Two-Step Synthesis of Hexahydropyrazino [1,2-α]-quinolines", Laboratory of Organic Chemistry, Twente University of Technology, Jul. 1987.

"The Aldol Condensation and Related Reactions". No year; no citation.

F. Babudri, et al., "Stereoselective synthesis of 2-alkylidene–3,4–dihydro–3–oxo–2H–1,4–benzothiazines", Tetrahedron vol. 38, No. 20, pp. 3059 to 3065, 1982.

PROCESS FOR THE PREPARATION OF 2-(4-ALKYL-1-PIPERAZINYL)-BENZALDEHYDE AND -BENZYLIDENYL COMPOUNDS

This application claims the benefit under 35 U.S.C. §119 of Provisional Application Serial No. 60/316,010, filed Aug. 30, 2001.

The present invention relates to a novel process for the preparation of compounds of formula I:

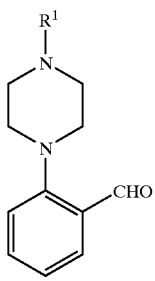

(I)

wherein $R^1$ is defined herein. The present invention also relates to the preparation of compounds of formula II:

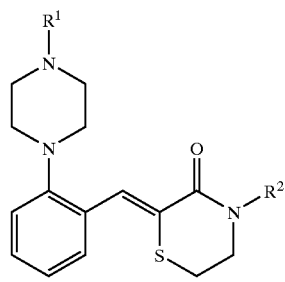

(II)

wherein $R^1$ and $R^2$ are as defined herein.

Other processes for making compounds of formula I have previously been described in International Patent Publication No. WO 98/14433, published Apr. 9, 1998, which is hereby incorporated by reference in its entirety. Previous methods employed in the art for making compounds of formula I are aryl-piperazine condensations described in Watthey et al., *J. Med. Chem.*, 1983, 26: 1116–1122 and Reinhoudt et al., *Synthesis*, 1987, 641–645. These aryl-piperazine condensations employ polar aprotic solvents, such as dimethyl sulfoxide or N,N-dimethylformamide, to obtain products of formula I in about 40 to 70% yield.

The method of the present invention represents a significant advance over these previously employed methods via the use of water as a solvent. The water solvent-based reaction affords not only higher yielding reactions, but also yields higher purity product and allows for easier product isolation. Water, of course, is a much more convenient solvent from a waste management and environmental viewpoint. Compounds of formula I are intermediates in the process for making compounds of formula II.

The compounds of formula II and pharmaceutically acceptable salts thereof, also described in International Patent Publication No. WO 98/14433, produced by the use of the processes of the present invention, are useful as selective agonists and antagonists of serotonin 1 (5-$HT_1$) receptors, specifically, of one or both of the 5-$HT_{1A}$ and 5-$HT_{1D}$ receptors. These compounds are useful in treating hypertension, all forms of depression (e.g., depression in cancer patients, depression in Parkinson's patients, post-myocardial infarction depression, subsyndromal symptomatic depression, depression in infertile women, pediatric depression, major depressive disorder, single episode depression, recurrent depression, child abuse induced depression, post partum depression, dysthymia; mild, moderate, or severe depressions with or without atypical features, melancholic features, psychotic features, catatonic features; seasonal affective disorder, geriatric depression, chronic depression; adjustment disorder with depressed mood or with anxiety and depressed mood; mixed anxiety and depression; substance induced mood disorder; and mood disorder secondary to a general medical condition), bipolar disorder (including in the depressed phase), generalized anxiety disorder, social anxiety, separation anxiety disorder, phobias (e.g., agoraphobia, social phobia and simple phobias), posttraumatic stress syndrome, avoidant personality disorder, premature ejaculation, eating disorders (e.g., binge eating disorder, anorexia nervosa and bulimia nervosa), obesity, chemical dependencies (e.g., addictions to alcohol, cocaine, heroin, phenobarbital, marijuana, nicotine and benzodiazepines), cluster headache, migraine, pain, Alzheimer's disease, obsessive-compulsive disorder; panic disorder with and without agoraphobia; memory disorders (e.g., dementia, amnestic disorders, and age-related cognitive decline (ARCD)), Parkinson's diseases (e.g., dementia in Parkinson's disease, neuroleptic-induced parkinsonism and tardive dyskinesias), endocrine disorders (e.g., hyperprolactinaemia), vasospasm (particularly in the cerebral vasculature), cerebellar ataxia, gastrointestinal tract disorders (involving changes in motility and secretion), negative symptoms of schizophrenia, premenstrual syndrome, fibromyalgia syndrome, stress incontinence, Tourette's syndrome, trichotillomania, kleptomania, male impotence, cancer (e.g. small cell lung carcinoma), chronic paroxysmal hemicrania, headache (associated with vascular disorders) autism, pervasive developmental disorder NOS, Asperger's disorder, selective mutism, chronic motor or vocal tic disorder, somatization disorder, insomnia, intermittent explosive disorder, pyromania, pathological gambling, impulse-control disorder, premenstrual dysphoric disorder, and attention-deficit/hyperactivity disorder (ADHD), and other disorders for which a 5-$HT_1$ agonist or antagonist is indicated.

SUMMARY OF THE INVENTION

The present invention relates to a process for the preparation of a compound of formula I:

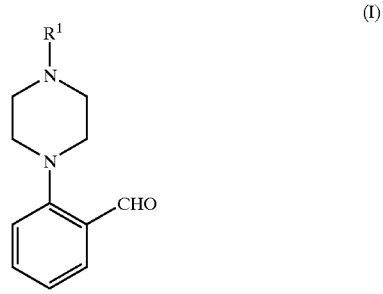

(I)

wherein $R^1$ is ($C_1$–$C_6$) alkyl; comprising the step of allowing a compound of formula III:

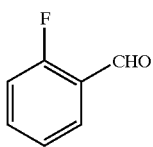

to react with a compound of formula IV:

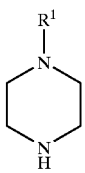

in the presence of water and a metal carbonate.

In a preferred embodiment of the invention, the molar ratio of the compound of formula IV to compound of formula III in the reaction is in the range of 1.0 to 2.0. In a more preferred embodiment, the ratio of the compound of formula IV to compound of formula III is approximately 1.8. The metal carbonate in the process of the invention is preferably an alkali metal carbonate, more preferably potassium or sodium carbonate, most preferably potassium carbonate. Preferably, the molar ratio of metal carbonate to compound of formula III is in the range of 2.0 to 1.2; more preferably, the molar ratio of the molar ratio of metal carbonate to compound of formula III is approximately 1.5. Preferably, the water volume present in the reaction is 4 ml to 30 ml per gram of 2-fluorobenzaldehyde of formula III; more preferably, 6 ml to 30 ml per gram of compound of formula III; most preferably, 8.0 ml per gram of compound of formula III.

In a preferred embodiment, the present invention relates to the process for the preparation of compounds of formula I wherein $R^1$ is methyl, ethyl or propyl.

In a more preferred embodiment, the present invention relates to the process for the preparation of compounds of formula I wherein $R^1$ is methyl.

The present invention further relates to a process for the preparation of the hydrochloride salt of the compound of formula I comprising reacting a compound formula I with an acyl chloride in aqueous alkanol or gaseous HCl dissolved in aqueous alkanol. Preferably, the acyl chloride is acetyl chloride and the alkanol is isopropanol.

The present invention also relates to a process for the preparation of compounds of formula II:

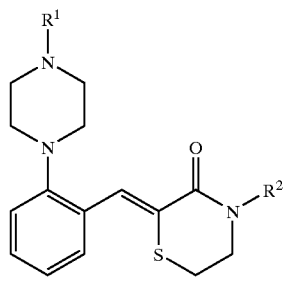

wherein $R^1$ is as defined above and $R^2$ is —$(CH_2)_m$B, wherein m is zero, one, two or three and B is phenyl or naphthyl, wherein each of the foregoing phenyl and naph-thyl groups may optionally be substituted with one or more substituents independently selected from chloro, fluoro, bromo, iodo, $(C_1-C_6)$alkyl, $(C_1-C_6)$alkoxy, $(C_1-C_6)$ alkoxy-$(C_1-C_6)$alkyl-, trifluoromethyl, trifluoromethoxy, and cyano; comprising the step of allowing the hydrochloride salt of the compound of formula I to react in the presence of a base in a suitable solvent with a compound of formula V:

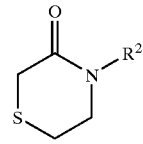

wherein $R^2$ is as defined above.

Preferably, the base used in the process for making the compound of formula II is an alkali metal hydroxide, an alkali metal hydride, alkali metal carbonate or an alkali metal alkylamine, or alkali metal amine; more preferably, the base is sodium hydride, lithium hydride, lithium hydroxide, sodium methoxide, lithium isopropoxide, potassium t-butoxide, lithium diisopropylamide; most preferably, the base is lithium hydroxide or sodium hydride, and even further preferred, the base is the monohydrate or anhydrous lithium hydroxide. Preferably, the suitable solvent for this step is isopropanol or toluene, more preferably, toluene.

In a preferred embodiment, the present invention relates to the process for the preparation of compounds of formula II wherein $R^2$ is phenyl optionally substituted with one or more substituents independently selected from chloro, fluoro, bromo, iodo, $(C_1-C_6)$alkyl, $(C_1-C_6)$alkoxy, $(C_1-C_6)$ alkoxy-$(C_1-C_6)$alkyl-, trifluoromethyl, trifluoromethoxy, and cyano.

In a more preferred embodiment, the present invention relates to the process for the preparation of compounds of formula II wherein $R^2$ is phenyl optionally substituted with one or more substituents independently selected from chloro, fluoro, bromo, or iodo.

In a most preferred embodiment, the present invention relates to the process for the preparation of compounds of formula II wherein $R^2$ is 3,4-dichlorophenyl.

The present invention also relates to a process for the preparation of a compound of formula II:

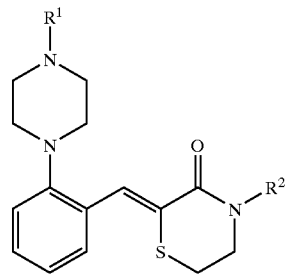

wherein $R^1$ is $(C_1-C_6)$ alkyl and $R^2$ is —$(CH_2)_m$B, wherein m is zero, one, two or three and B is phenyl or naphthyl, wherein each of the foregoing phenyl and naphthyl groups may optionally be substituted with one or more substituents independently selected from chloro, fluoro, bromo, iodo, $(C_1-C_6)$alkyl, $(C_1-C_6)$alkoxy, $(C_1-C_6)$ alkoxy-$(C_1-C_6)$alkyl-, trifluoromethyl, trifluoromethoxy, and cyano; comprising the steps of (i) allowing a compound of formula III:

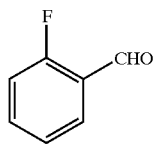

(III)

to react with a compound of formula IV:

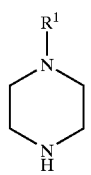

(IV)

in the presence of water and a metal carbonate;

(ii) reacting the compound formula I:

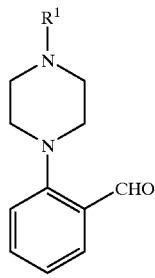

(I)

wherein $R^1$ is defined above, as formed in step (i), with an acyl chloride or gaseous hydrochloric acid dissolved in an aqueous alkanol;

(iii) reacting the hydrochloride salt of the compound of formula I formed in step (ii) in the presence of a base in a suitable solvent with a compound of formula V:

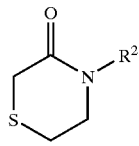

(V)

wherein $R^2$ is defined above.

Preferably, in this three-step process, $R^1$ is methyl and $R^2$ is 3,4-dichlorophenyl group. In addition, it is preferred that the metal carbonate in step (i) is an alkali metal carbonate, more preferably potassium or sodium carbonate, most preferably potassium carbonate. Preferably, in step (i), the molar ratio of metal carbonate to compound of formula III is in the range of 2.0 to 1.2; more preferably, the molar ratio of the molar ratio of metal carbonate to compound of formula III is approximately 1.5.

Preferably, in step (ii), the acyl chloride is used and is preferably acetyl chloride and the alkanol is isopropanol. Preferably, in step (iii), the base used in the process for making the compound of formula II is sodium hydride, lithium hydride, lithium hydroxide, sodium methoxide, lithium isopropoxide, potassium t-butoxide, lithium diisopropylamide; most preferably, the base is lithium hydroxide or sodium hydride, and even further preferred, the base is the monohydrate or anhydrous lithium hydroxide. Preferably, the suitable solvent for this step is isopropanol or toluene, more preferably, toluene.

The present invention also relates to the preparation of the citric acid salt of a compound of formula II comprising the steps of mixing a compound of formula II and citric acid in a suitable solvent. Preferably, the suitable solvent is an $(C_1-C_6)$alkanol; more preferably, isopropanol.

The term "alkyl", as used herein, unless otherwise indicated, includes saturated monovalent hydrocarbon radicals having straight, branched or cyclic moieties or combinations thereof. The term "halo" or "halogen", as used herein, unless otherwise indicated, means fluorine, chlorine, bromine or iodine.

The term "suitable solvent", as used herein, unless otherwise indicated, means a medium which serves to largely dissolve particular indicated substance(s), compound(s) or reagent(s) to form a uniformly dispersed mixture of that substance or compound at the molecular or ionic level.

The term "pharmaceutically acceptable salt", as used herein, unless otherwise indicated, refers to an acid addition salt of a proton acid, as defined herein, or a hydrate of an acid addition salt. The term "proton acid" used to prepare acid addition salts of the compounds of the process of this invention are those which form non-toxic acid addition salts, i.e., salts containing pharmacologically acceptable anions, such as the hydrochloride, hydrobromide, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate (i.e., 1,1'-methylene-bis-(2-hydroxy-3-naphthoate)) salts.

"Treating" refers to, and includes, reversing, alleviating, inhibiting the progress of, or preventing, a disease, disorder or condition, or one or more symptoms thereof; and, "treatment" and "therapeutically" refer to the act of treating, as defined above.

DETAILED DESCRIPTION OF THE INVENTION

The present invention comprises an improvement in the process for the preparation of compounds of formula I that permits the use of water as the solvent in the place of organic solvents, such as dimethyl sulfoxide (DMSO), N,N-dimethylformamide (DMF), N,N-dimethylacetamide (DMA) or N-methyl-2-pyrrolidinone (NMP), previously used to make such compounds. Unless otherwise indicated, the variables $R^1$ and $R^2$ are as described above.

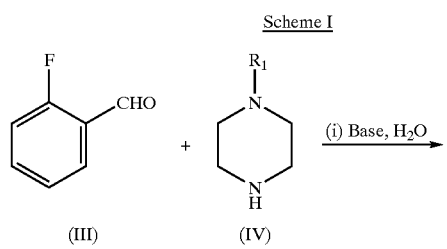

Scheme I (III)  (IV)

between 6 and 12 ml per gram; most preferably about 8 ml per gram. The reaction is carried out at reflux (100–105° C.) and monitored by a technique such as HPLC until complete, then cooled and extracted with an organic solvent, such as methylene chloride. Interestingly, when compounds, such as 2-chlorobenzaldehyde or 3-fluorobenzaldehyde, are used in place of 2-fluorobenzaldehyde under the above-noted reaction conditions, these compounds remain unreacted and no addition product is detected in the reaction mixture. However, the 4-fluorobenzaldehyde compound reacts to produce a substitution product in high yield under similar conditions (See Example 2).

In Table 1 is set forth a number of reaction conditions for the process of the invention using methylpiperazine as the compound of formula IV. The highest yields are most evident from the use of sodium and potassium carbonate as the water soluble base. Based on the molar equivalents of compounds of formula III, the reaction is best carried out with 1.5 to 2.0 equivalents of methylpiperazine and about 1.5 equivalents of carbonate salt.

TABLE 1

Preparation of Compound of Formula I.

| Base | (IV) ($R^1$ = Me) | (III) | Water (mL/g(III)) | Time (h) | Temp (° C.) | Yield |
|---|---|---|---|---|---|---|
| $Na_2CO_3$(1.5) | 1.8 | 1.0 | 8.0 | 23.5 | 102 | 96% |
| $Na_2CO_3$(1.5) | 1.5 | 1.0 | 10.0 | 20 | 100 | 96% |
| NaOH(1.5) | 2.0 | 1.0 | 12.0 | 18 | 100 | 30% |
| NaOH(1.5) | 2.0 | 1.0 | 8.0 | 17 | 102 | Oil~89% |
| $Na_2CO_3$(1.0) | 2.0 | 1.0 | 8.0 | 20 | 102 | 94% |
| $Na_2CO_3$(1.5) | 4.0 | 1.0 | Neat (no $H_2O$) | 19.5 | 115–120 | 7% |
| $K_2CO_3$(1.5) | 1.8 | 1.0 | 8.0 | 22.5 | 100–104 | 96% |
| $K_2CO_3$(1.5) | 1.8 | 1.0 | 8.0 | 21 | 100–103 | 96% |

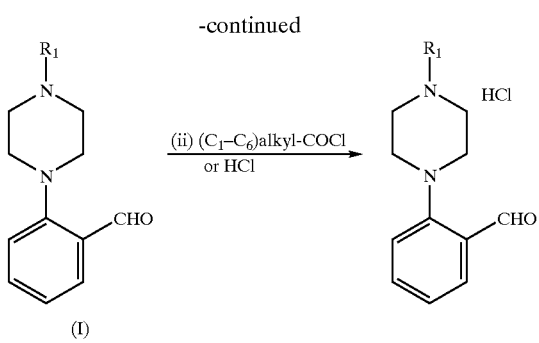

-continued (ii) $(C_1-C_6)$alkyl-COCl or HCl (I)

Referring to Scheme 1, in step (i), a compound of formula III and a compound of formula IV is allowed to react in the presence of a water-soluble base in water solvent. Preferably, a stoichiometric ratio of compound of formula IV to compound of formula III of 1.0 to 2.0, more preferably about 1.8, is used in the reaction. Preferably, the water-soluble base is a metal carbonate, more preferably an alkali metal carbonate, most preferably, potassium carbonate. Further, a stoichiometric ratio of metal carbonate to compound of formula III of 1.0 to 1.5 is preferred; more preferably, a ratio of 1.5 is used in the reaction. In addition, the water volume in the reaction is preferably between 4 and 30 ml per gram of compound of formula III; more preferably Step (ii) of Scheme 1 is the preparation of the hydrochloride salt of the compound of formula I (formula I'). The compound of formula I is dissolved in an aqueous alkanolic solvent, preferably aqueous isopropanol, more preferably less then 5% aqueous isopropanol, most preferably 1.0% aqueous isopropanol, at ambient temperature. The acyl chloride, $((C_1-C_6)$alkyl-COCl), preferably acetyl chloride, is added to the solution. A stoichiometric ratio of acyl chloride to compound of formula I of 1.0 to 1.5 is preferably used in this step. The reaction mixture forms a slurry and is then cooled to about 0° C., then granulated and filtered. Alternatively, the hydrochloride salt of the compound of formula I can be prepared by dissolving approximately 1.0 equivalent of gaseous HCl in <1.0% aqueous isopropanol or ethyl acetate.

Other water-soluble salts of compounds of formula I may be formed via the reaction of the compound of formula I with the acid in a suitable solvent, such as tetrahydrofuran. Although the yields are quite good, the hydrochloride salts of the compound of formula I works best in the reaction conditions designed for the preparation of compounds of formula II.

TABLE 2

Preparation of Citric, p-Toluenesulfonic Acid and Mesylate Salts of Compounds of Formula I.

| Acid | Cmpd (I) | Solvent (L/kg (I)) | Time (h) | Temp ° C. | Isolated Yield |
|---|---|---|---|---|---|
| Citric (1.0) | 1.0 | THF (22) | 16 | 20–25 | 98% |
| p-TSA (1.0) | 1.0 | THF (15) | 1 | 20–25 | 82% |
| MsOH (1.0) | 1.0 | THF (15) | 1 | 20–25 | 83% |

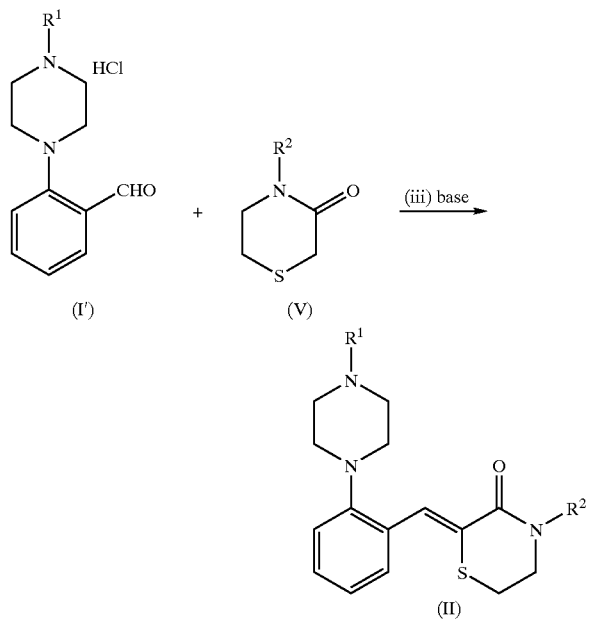

Scheme II

Referring to Scheme II, compounds of formula I are converted into compounds of the formula II, by subjecting them to aldol condensation conditions (step (iii)). In the aldol condensation, a compound of the formula I', the hydrochloride salt of the compound of formula I, wherein $R^1$ is as defined above, is reacted with a compound of the formula V, where $R^2$ is defined above, in the presence of a base. The water removal techniques may involve the use of molecular sieves or a Dean-Stark trap to isolate the water created as an azeotrope with the solvent. The aldol reaction is typically carried out in a polar solvent such as DMSO, DMF, tetrahydrofuran (THF), THF/triethylamine, isopropanol, methanol or ethanol, at a temperature from about −78° C. to about 80° C. Suitable bases for use in the aldol formation step include alkali metal hydroxides, hydrides, carbonates or alkylamines, or amines themselves, more preferably, the base used is sodium hydride, lithium hydride, lithium hydroxide, sodium methoxide, lithium isopropoxide, potassium t-butoxide, lithium diisopropylamide; most preferably, the base is lithium hydroxide or sodium hydride, and even further preferred, the base is the monohydrate or anhydrous lithium hydroxide. Preferably, the suitable solvent for this step is isopropanol or toluene, more preferably, toluene. Aldol condensations are described in "Modern Synthetic Reactions," Herbert O. House, 2d. Edition, W. A. Benjamin, Menlo Park, Calif., 629–682 (1972) and Tetrahedron, 38 (20), 3059 (1982).

After the aldol reaction is complete as confirmed by, e.g., TLC, HPLC, or any other suitable detection method, the reaction mixture is optimally cooled to 0–5° C., granulated for 1 to 2 hours and then filtered. The solvent-wet cake is slurried in water and the pH adjusted to about 7–8 via addition of concentrated HCl. The slurry that forms can be cooled, granulated, and then filtered to yield the product.

As noted above, when the preferred base, lithium hydroxide monohydrate, is used, the stoichiometry can be varied in the range of 1.2 to 5.0 equivalents of lithium hydroxide to reactants, but the reaction completion times will vary. The aldol reaction appears to be catalytic in lithium hydroxide. It is noteworthy that when potassium hydroxide is used to catalyze the aldol reaction between compounds of formula I' and compounds of formula V wherein $R^2$ is dichlorophenyl, in isopropanol, yields are significantly reduced. Potassium hydroxide appears to favor the hydrolysis of thiomorpholinone ring as the major side reaction. Once the compound of formula II is prepared, pharmaceutically acceptable acid addition salts thereof may be formed via their reaction with appropriate proton acids, particularly preferred is the citric acid addition salt of the compound of formula II.

The preparation of other compounds of the present invention not specifically described in the foregoing experimental section can be accomplished using combinations of the reactions described above that will be apparent to those skilled in the art.

In each of the reactions discussed or illustrated in Schemes I and II above, pressure is not critical, unless otherwise indicated. Pressures from about 0.9 atmospheres to about 2 atmospheres are generally acceptable and ambient pressure, i.e., about 1 atmosphere, is preferred as a matter of convenience.

This invention is also directed to processes of the invention employing isotopically-labeled compounds identical to those recited in formula I or II, or pharmaceutically acceptable salts thereof, but for the fact that one or more atoms are replaced therein by an atom having an atomic mass or mass number different from the atomic mass or mass number usually abundantly found in nature. Examples of isotopes that can be incorporated into compounds or salts thereof of this invention include isotopes of hydrogen, carbon, nitrogen, oxygen, phosphorous, fluorine and chlorine, such as $^2H$, $^3H$, $^{13}C$, $^{14}C$, $^{15}N$, $^{18}O$, $^{17}O$, $^{31}P$, $^{32}P$, $^{35}S$, $^{18}F$ and $^{36}Cl$, respectively.

Processes using certain isotopically-labeled compounds of the present invention, for example those into which radioactive isotopes such as $^3H$ and $^{14}C$ are incorporated, are useful, for example, in providing compounds for use in drug and/or substrate tissue distribution assays. Tritiated, i.e., $^3H$, and carbon-14, i.e., $^{14}C$, isotopes are particularly preferred for their ease of preparation and detectability. Furthermore, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances.

The activity, methods for testing activities, dosages, dosage forms, methods of administration and background information concerning the compounds of formula II are set forth in International Patent Publication No. WO 98/14433, published Apr. 9, 1998. The compounds of formula II pharmaceutically acceptable salts thereof prepared using the methods of the present invention exhibit significant agonist and antagonist activity towards the serotonin-1 receptors and are of value in the treatment of a wide variety of clinical conditions as set forth above.

The active compounds of formula II and pharmaceutically acceptable salts thereof may be administered via either oral, parenteral (e.g., intravenously, intramuscularly or subcutaneously), transdermal or topical routes to mammals. The compositions of the present invention may be formulated in a conventional manner using one or more pharmaceutically acceptable carriers. Thus, the active compounds of the invention may be formulated for oral, buccal, intranasal, parenteral (e.g., intravenous, intramuscular or subcutaneous) or rectal administration or in a form suitable for administration by inhalation or insufflation.

For oral administration, the pharmaceutical compositions may take the form of, for example, tablets or capsules prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium phosphate); lubricants (e.g., magnesium stearate, talc or silica); disintegrants (e.g., potato starch or sodium starch glycolate); or wetting agents (e.g., sodium lauryl sulfate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, methyl cellulose or hydrogenated edible fats); emulsifying agents (e.g., lecithin or acacia); non-aqueous vehicles (e.g., almond oil, oily esters or ethyl alcohol); and preservatives (e.g., methyl or propyl p-hydroxybenzoates or sorbic acid).

The active compounds of the invention may be formulated for parenteral administration by injection, including using conventional catheterization techniques or infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulating agents such as suspending, stabilizing and/or dispersing agents. Alternatively, the active ingredient may be in powder form for reconstitution with a suitable vehicle, e.g., sterile pyrogen-free water, before use.

The active compounds of the invention may also be formulated in rectal compositions such as suppositories or retention enemas, e.g., containing conventional suppository bases such as cocoa butter or other glycerides.

For intranasal administration or administration by inhalation, the active compounds of the invention are conveniently delivered in the form of a solution or suspension from a pump spray container that is squeezed or pumped by the patient or as an aerosol spray presentation from a pressurized container or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. The pressurized container or nebulizer may contain a solution or suspension of the active compound. Capsules and cartridges (made, for example, from gelatin) for use in an inhaler or insulator may be formulated containing a powder mix of a compound of the invention and a suitable powder base such as lactose or starch.

A proposed dose of the active compounds of the invention for oral, parenteral or buccal administration to the average adult human for the treatment of the conditions referred to above (e.g., depression) is 0.1 to 200 mg of the active ingredient per unit dose which could be administered, for example, 1 to 4 times per day. Aerosol formulations for treatment of the conditions referred to above (e.g., migraine) in the average adult human are preferably arranged so that each metered dose or "puff" of aerosol contains 20 $\mu$g to 1000 $\mu$g of the compound of the invention. The overall daily dose with an aerosol will be within the range 100 $\mu$g to 10 mg. Administration may be several times daily, for example 2, 3, 4 or 8 times, giving for example, 1, 2 or 3 doses each time.

In connection with the use of an active compound of this invention with a 5-HT re-uptake inhibitor, preferably sertraline, for the treatment of subjects possessing any of the above conditions, it is to be noted that these compounds may be administered either alone or in combination with pharmaceutically acceptable carriers by either of the routes previously indicated, and that such administration can be carried out in both single and multiple dosages. More particularly, the active combination can be administered in a wide variety of different dosage forms, i.e., they may be combined with various pharmaceutically-acceptable inert carriers in the form of tablets, capsules, lozenges, troches, hard candies, powders, sprays, aqueous suspension, injectable solutions, elixirs, syrups, and the like. Such carriers include solid diluents or fillers, sterile aqueous media and various non-toxic organic solvents, etc. Moreover, such oral pharmaceutical formulations can be suitably sweetened and/or flavored by means of various agents of the type commonly employed for such purposes. In general, the compounds of formula I are present in such dosage forms at concentration levels ranging from about 0.5% to about 90% by weight of the total composition, i.e., in amounts which are sufficient to provide the desired unit dosage and a 5-HT re-uptake inhibitor, preferably sertraline, is present in such dosage forms at concentration levels ranging from about 0.5% to about 90% by weight of the total composition, i.e., in amounts which are sufficient to provide the desired unit dosage.

A proposed daily dose of an active compound of this invention in the combination formulation (a formulation containing an active compound of this invention and a 5-HT re-uptake inhibitor) for oral, parenteral, rectal or buccal administration to the average adult human for the treatment of the conditions referred to above is from about 0.01 mg to about 2000 mg, preferably from about 0.1 mg to about 200 mg of the active ingredient of formula I per unit dose which could be administered, for example, 1 to 4 times per day.

EXAMPLES

The present invention is illustrated by the following examples. It will be understood, however, that the invention is not limited to the specific details of these examples.

Example 1

2-(4-Methyl-1-piperazinyl)benzaldehyde

Potassium carbonate (8.3 g, 60 mmol) and 1-methylpiperazine (7.2 g, 72 mmol) were dissolved in 40 mL of water and then 2-fluorobenzaldehyde (5.0 g, 40 mmol) was added. The mixture was heated at reflux (100–104° C.) under a nitrogen atmosphere for 22.5 hours when HPLC showed that the reaction was complete. The solution was cooled to 20–25° C. and then extracted with methylene chloride (2×40 mL). The methylene chloride extracts were combined, washed with water (2×50 mL), and then concentrated at reduced pressure to a yellow oil (7.8 g, 96% yield). $^1$H NMR (CDCl$_3$) showed that the yellow oil was essentially pure title compound and the $^1$H NMR spectrum was consistent with literature values (Walters et al., *Synthesis*, 1987: 641). $^{13}$C NMR (CDCl$_3$) δ 191.70, 135.25, 129.94, 128.84, 122.84, 119.23, 55.34, 54.20, and 46.33.

Example 2

4-(4-Methyl-1-piperazinyl)benzaldehyde

Potassium carbonate (3.3 g, 24 mmol) and 1-methylpiperazine (2.8 g, 29 mmol) were dissolved in 16 mL of water and then 4-fluorobenzaldehyde (2.0 g, 16 mmol) was added. The mixture was heated at reflux (100–103° C.) under a nitrogen atmosphere for 21 hours when HPLC showed that the reaction was complete. The solution was cooled to 20–25° C. and then extracted with methylene chloride (2×30 mL). The methylene chloride extracts were combined, washed with water (2×30 mL), and then concentrated at reduced pressure to a yellow oil (3.1 g, 96% yield). The crude solid was triturated with hexanes to afford crystals. mp 60.5–62.0° C. $^1$H NMR (CDCl$_3$) δ 9.77 (s, 1H), 7.74 (d, J=10 Hz, 2H), 6.91 (d, J=10 Hz, 2H), 3.40 (m, 4H), 2.53 (m, 4H), and 2.34 (s, 3H).

Example 3

2-(4-Methyl-1-piperazinyl)benzaldehyde hydrochloride 2-(4-Methyl-1-piperazinyl)benzaldehyde (7.8 g, 38 mmol) was dissolved in 0.1% aqueous isopropanol (62 mL) at 20–25° C. under a nitrogen atmosphere and then 2.8 mL (40 mmol) of neat acetyl chloride was slowly added. The resulting slurry was cooled to 0–5° C., granulated for 1 hour, and then filtered. The cake was washed with cold (0–5° C.) isopropanol (8 mL) followed by hexanes (16 mL) and then dried in vacuo at 25–30° C. The title compound (7.9 g, 83% yield) was obtained as a light yellow solid. If desired, the title compound can be recrystallized from refluxing isopropanol (6 L/kg of solid) to afford rod-like crystals (mp 225–226° C.) which were recovered in 93% yield. $^1$H NMR (CDCl$_3$) δ 12.3 (s, 1H), 10.1 (s, 1H), 7.71 (m, 1H), 7.69 (m, 1H), 7.15 (m, 1H), 7.05 (m, 1H), 3.62 (m, 2H), 3.51 (m 2H), 3.26 (m, 4H), and 2.86 (s, 3H). $^{13}$C NMR (CDCl$_3$) δ 191.24, 152.24, 135.70, 134.30, 128.55, 124.03, 119.75, 54.00, 49.94 and 43.74. Anal. Calcd for C$_{12}$H$_{16}$N$_2$O HCl: C, 59.87; H, 7.12; N, 11.64. Found: C, 59.98; H, 7.23; N, 11.65.

In the above procedure, 1.0–1.5 equivalents of acetyl chloride has been successfully used to obtain the title compound in 89–90% isolated yields in excellent quality. Alternatively, the title compound can be prepared in 91% yield from 1.0 equivalent of gaseous HCl dissolved in 0.1% aqueous isopropanol or 96% yield from 1.0 equivalent of gaseous HCl dissolved in ethyl acetate. The quality of the salts prepared using gaseous HCl was comparable to the acetyl chloride method.

Example 4

(Z)-4-(3,4-Dichlorophenyl)-2-[2-(4-methyl-1-piperazinyl)-benzylidenyl]-3-thiomorpholinone A. Under a nitrogen atmosphere, 2-(4-methyl-1-piperazinyl)-benzaldehyde hydrochloride (25.0 g, 104 mmol), 4-(3,4-dichlorophenyl)-3-thiomorpholinone (27.3 g, 104 mmol), and anhydrous lithium hydroxide (7.5 g, 313 mmol) were added to 100 mL of isopropanol. The mixture was stirred and heated at 35–40° C. for 41 hours when HPLC indicated that the reaction was complete. The mixture was cooled to 20–25° C. and 100 mL of water was added. The pH was adjusted to 7–8 by addition of concentrated HCl. The slurry was cooled to 0–5° C., granulated for 2 hours, and then filtered. The cake was washed with 50 mL of an isopropanol/water (1:1) mixture and then air-dried at ambient temperature to give 38.3 g (82% yield) of yellow needles mp 166.5–167° C. The spectral and physical properties of yellow needles were identical to an authentic sample.

B. 2-(4-Methyl-1-piperazinyl)benzaldehyde hydrochloride (25.0 g, 104 mmol), 4-(3,4-dichlorophenyl)-3-thiomorpholinone (27.3 g, 104 mmol), lithium hydroxide monohydrate (6.55 g, 156 mmol) and toluene (75 mL) were combined under a nitrogen atmosphere and then heated to reflux (110–112° C.). Water was continually removed from the cooled toluene/water azeotrope by the use of a Dean Stark apparatus. The reaction mixture was heated at reflux for 20.5 hours when HPLC indicted that the reaction was complete. The mixture was cooled to 0–5° C. and 12.5 mL of toluene was added to facilitate stirring. The slurry was granulated for 2 hours at 0–5° C., filtered, and the cake washed with 25 mL of cold toluene. The isolated solid was suspended in 400 mL of water and the pH of the slurry was adjusted to 7–8 by the addition of concentrated HCl. The solid was filtered, washed with 100 mL of water and then dried at ambient temperature to a constant weight to give 42.1 g (90% yield) of pure title compound.

C. A suspension of 60% NaH in mineral oil (195 mg, 4.8 mmol) was added to 4 mL of THF under a nitrogen atmosphere and then the NaH/THF mixture was slowly added over 20 minutes to a solution of 2-(4-methyl-1-piperazinyl) benzaldehyde (0.82 g, 4.0 mmol) and 4-(3,4-dichlorophenyl)-3-thiomorpholinone (1.1 g, 4.0 mmol) in 9 mL of THF maintained under nitrogen. The mixture was warmed to 30–35° C. and H$_2$ gas was liberated over 30 minutes. The mixture was heated an additional 30 minutes at 30–35° C. and then cooled to room temperature and quenched with water (20 mL). The pH was adjusted to 1.8 with 9 mL of 1N HCl to give a solution which was stirred for 2 hours at 20–25° C. The pH was adjusted to about 7.7 with 1N NaOH to precipitate a fluid yellow slurry. The solid was granulated for 2 hours at 20–25° C., cooled to 0–5° C., and filtered. After the solid was washed with water (5 mL), it was dried in vacuo at 40° C. to afford 1.6 g of yellow needles of the title compound (89% yield).

D. At 20–25° C. under a nitrogen atmosphere, triethylamine (4.2 g, 41.7 mmol) was added to a stirred suspension of 2-(4-methyl-1-piperazinyl)benzaldehyde hydrochloride (10.0 g, 41.7 mmol) in 100 mL of dry THF. The slurry was stirred for 1 hours at room temperature and then filtered. 4-(3,4-Dichlorophenyl)-3-thiomorpholinone (11.1 g, 42.4 mmol) and a 2.0 g of 60% suspension of NaH (50.3 mmol, 1.2 equivalents) in mineral oil were added to the THF filtrate at 20–25° C. Some hydrogen liberation occurred upon addition of NaH. After the mixture was warmed to 30–35° C., the temperature was maintained for 2 hours when HPLC showed that the reaction was complete and hydrogen evolution had stopped. The solution was cooled to room temperature and 340 mL of water was added. The pH was adjusted to approximately 7.5 with 6N HCl to give a slurry which was stirred for 1 hour at 0–5° C. The solid was filtered, washed with water and then dried at 40° C. overnight under reduced pressure. Pure yellow needles of the title compound (14.8 g, 80% yield) were obtained.

Example 5

(Z)-4-(3,4-dichlorophenyl)-2-[2-(4-methylpiperazin-1-yl)-benzylidene]-thiomorpholin-3-one citrate To an appropriate speck-free flask maintained under a nitrogen atmosphere, add Z-4-(3,4-dichlorophenyl)-2-[2-(4-methylpiperazin-1-yl)-benzylidene]-thiomorpholin-3-one (23.2 g, 51.8 mmol), citric acid (10.4 g, 54.4 mmol), and 603 mL of a speck-free aqueous isopropanol solution (1:1 v/v). A slurry formed and was heated to reflux (83–84° C.) affording a solution at approximately 70° C. The solution was further heated at reflux for 0.5 hours and then filtered hot. The filtrate was slowly cooled to 50–55° C. over 0.45 hours and then maintained at 50–55° C. for 1 hour. The slurry was cooled further to 0–5° C., granulated for 1–2 hours, and then filtered. The white crystalline solid was washed with 50% aqueous isopropanol (50 mL) and then dried at reduced pressure overnight to afford 29.1 grams of the title compound (88% yield).

What is claimed is:

1. A process for the preparation of a compound of formula I:

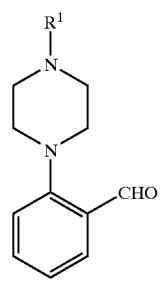

(I)

wherein $R^1$ is ($C_1$–$C_6$) alkyl; comprising the step of allowing a compound of formula III:

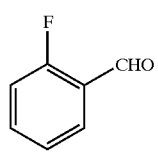

(III)

to react with a compound of formula IV:

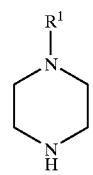

(IV)

in the presence of water and a metal carbonate.

2. A process according to claim 1 wherein the molar ratio of the compound of formula IV to compound of formula III in the reaction is in the range of 1.0 to 2.0.

3. A process according to claim 1 wherein the molar ratio of the compound of formula IV to compound of formula III is approximately 1.8.

4. A process according to claim 1 wherein the metal carbonate in the process of the invention is preferably an alkali metal carbonate.

5. A process according to claim 4 wherein the alkali metal carbonate is potassium carbonate or sodium carbonate.

6. A process according to claim 1 wherein the molar ratio of metal carbonate to compound of formula III is in the range of 2.0 to 1.2.

7. A process according to claim 1 wherein $R^1$ is methyl, ethyl or propyl.

8. A process according to claim 1 wherein the water volume is between 4 and 30 ml per gram compound of formula III.

9. A process according to claim 1 further comprising the step of reacting a compound formula I with an acyl chloride or gaseous HCl dissolved in aqueous alkanol to prepare the hydrochloride salt of the compound of formula I.

10. A process according to claim 9 further comprising the step of allowing the hydrochloride salt of the compound of formula I to react in the presence of a base in a suitable solvent with a compound of formula V:

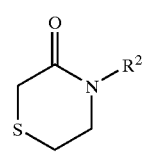

(V)

wherein $R^2$ is —$(CH_2)_m$B, wherein m is zero, one, two or three and B is phenyl or naphthyl, wherein each of the foregoing phenyl and naphthyl groups may optionally be substituted with one or more substituents independently selected from chloro, fluoro, bromo, iodo, ($C_1$–$C_6$)alkyl, ($C_1$–$C_6$)alkoxy, ($C_1$–$C_6$) alkoxy-($C_1$–$C_6$)alkyl-, trifluoromethyl, trifluoromethoxy, and cyano;

to prepare a compound of formula II:

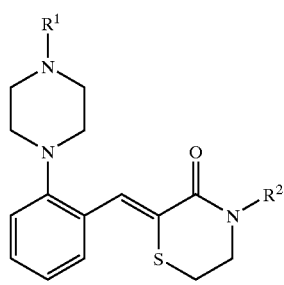
(II)

wherein $R^1$ is $(C_1-C_6)$ alkyl and $R^2$ is as defined above.

11. A process according to claim 10 wherein the base is an alkali metal hydroxide, an alkali metal hydride, alkali metal carbonate, an alkali metal alkylamine or alkali metal amine.

12. A process according to claim 10 wherein the base is sodium hydride, lithium hydride, lithium hydroxide, sodium methoxide, lithium isopropoxide, potassium t-butoxide, lithium diisopropylamide.

13. A process according to claim 10 wherein the base is the monohydrate of lithium hydroxide or anhydrous lithium hydroxide.

14. A process according to claim 10 wherein the suitable solvent is isopropanol or toluene.

15. A process for the preparation of a compound of formula II:

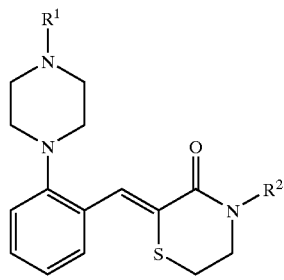
(II)

wherein $R^1$ is $(C_1-C_6)$ alkyl and $R^2$ is —$(CH_2)_m$B, wherein m is zero, one, two or three and B is phenyl or naphthyl, wherein each of the foregoing phenyl and naphthyl groups may optionally be substituted with one or more substituents independently selected from chloro, fluoro, bromo, iodo, $(C_1-C_6)$alkyl, $(C_1-C_6)$alkoxy, $(C_1-C_6)$ alkoxy-$(C_1-C_6)$ alkyl-, trifluoromethyl, trifluoromethoxy, and cyano; comprising the steps of (i) allowing a compound of formula III:

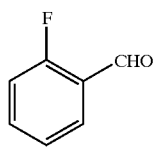
(III)

to react with a compound of formula IV:

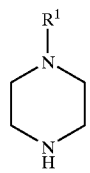
(IV)

in the presence of water and a metal carbonate;

(ii) reacting a compound of formula I:

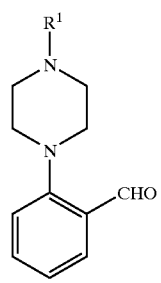
(I)

wherein $R^1$ is defined above as formed in step (i) with an acyl chloride or hydrochloric acid dissolved in an aqueous alkanol;

(iii) reacting the hydrochloride salt of the compound of formula I formed in step (ii) in the presence of a base in a suitable solvent with a compound of formula V:

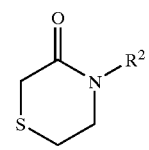
(V)

wherein $R^2$ is defined above.

16. A process according to claim 15 wherein $R^1$ is methyl and $R^2$ is 3,4-dichlorophenyl group.

17. The process according to claim 15 further comprising the step of mixing a compound of formula II and citric acid in a suitable solvent to form a citric acid salt.

18. The process according to claim 17 wherein $R^1$ is methyl and $R^2$ is a 3,4-dichlorophenyl group.

19. The process according to claim 17 wherein the suitable solvent is an $(C_1-C_6)$alkanol or isopropanol.

20. The citric acid salt of a compound of formula II, wherein $R^1$ and $R^2$ are defined as in claim 17, made according to the process of claim 17.

21. The citric acid salt according to claim 20 wherein $R^1$ is methyl and $R^2$ is 3,4-dichlorophenyl group.

* * * * *